United States Patent
Sakanoue et al.

(10) Patent No.: US 6,875,841 B2
(45) Date of Patent: Apr. 5, 2005

(54) POLYOXYALKYLENE DERIVATIVE AND PROCESS OF PRODUCING THE SAME

(75) Inventors: Kenji Sakanoue, Kawasaki (JP); Kazuhiro Kubo, Kawasaki (JP); Syunsuke Ohashi, Yokohama (JP); Chika Itoh, Kawasaki (JP)

(73) Assignee: NOF Corporation, Tokyo (JP)

(*) Notice: Subject to any disclaimer, the term of this patent is extended or adjusted under 35 U.S.C. 154(b) by 141 days.

(21) Appl. No.: 10/206,955

(22) Filed: Jul. 30, 2002

(65) Prior Publication Data

US 2003/0065134 A1 Apr. 3, 2003

(30) Foreign Application Priority Data

Jul. 31, 2001 (JP) ........................................ 2001-232045

(51) Int. Cl.⁷ .............................................. C08G 65/34
(52) U.S. Cl. ........................ 528/425; 528/423; 528/491; 528/492; 528/502 R
(58) Field of Search ................................ 528/425, 423, 528/491, 492, 502 R

(56) References Cited

U.S. PATENT DOCUMENTS

| 6,017,943 A | 1/2000 | Acharya et al. |
| 2001/0044526 A1 | 11/2001 | Shen |

FOREIGN PATENT DOCUMENTS

| EP | 0 273 545 A1 | 7/1988 |
| EP | 0 318 162 A2 | 5/1989 |
| EP | 0 839 849 A1 | 5/1989 |
| JP | 2000-191700 A | 7/2000 |
| WO | WO 92/16221 A1 | 10/1992 |
| WO | WO 99/03887 A1 | 1/1999 |
| WO | WO 01/62827 A2 | 8/2001 |

OTHER PUBLICATIONS

Yasuo Tsutsumi, et al., "Site–specific chemical modification with polyethylene glycol of recombinant immunotoxin anti–Tac(Fv)–PE38(LMB–2) improves antitumor activity and reduces animal toxicity and immunogenicity", Proc. National Science, vol. 97, No. 15 (Jul. 18, 2000).

Hsio–Huei Wu, et al., "p53 protein oxidation in cultured cells in response to pyrrolidine dith ocarbarnate: a novel method for relating the amount of p53 oxidation in vivo to the regulation of p53–responsive genes", Biochem. J. 351, 87–93 (2000).

Timothy P. Kogan, "The Synthesis of Substituted Methoxy–Poly (Ethyleneglycol) Derivatives Suitable for Selective Protein Modification", Synthetic Communications, 22(16), 2417–2424 (1992).

Patent Abstracts of Japan—08165343 (Jun. 25, 1996).

European Search Report dated Nov. 29, 2002.

*Primary Examiner*—Duc Truong
(74) *Attorney, Agent, or Firm*—Sughrue Mion, PLLC

(57) ABSTRACT

A polyoxyalkylene derivative is represented by formula (I):

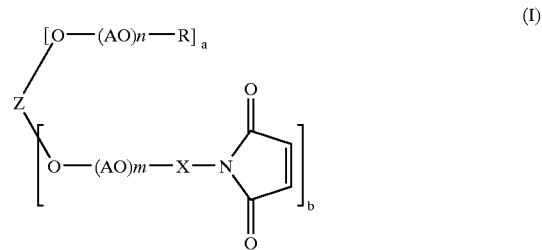

wherein Z represents a residue of a compound having 2 to 8 hydroxyl groups; AO represents an oxyalkylene group having 2 to 18 carbon atoms; n and m each represent an integer of 0 to 2000 provided that both n and m do not represent 0; a and b each represent an integer satisfying the relationships: $2 \leq a+b \leq 8$ and $1 \leq b$; R represents a hydrocarbon group having 1 to 30 carbon atoms; and X represents a divalent hydrocarbon group having 3 to 10 carbon atoms.

15 Claims, No Drawings

POLYOXYALKYLENE DERIVATIVE AND PROCESS OF PRODUCING THE SAME

BACKGROUND OF THE INVENTION

1. Field of the Invention

This invention relates to a polyoxyalkylene derivative and a process of producing the same. More particularly, it relates to a polyoxyalkylene derivative useful for modification of biological substances, such as polypeptides, physiologically active proteins, enzymes, and modification of drug delivery systems (hereinafter DDS) such as liposomes and polymeric micelles.

2. Description of the Related Art

Terminal modified polyoxyalkylene compounds have recently been engaging attention as an important carrier for DDS. In particular, modification of polypeptides, physiologically active proteins, enzymes, etc. with a polyoxyalkylene compound and modification of liposomes, polymeric micelles, etc. with a polyoxyalkylene compound produce such effects as reduction of antigenicity (immunoreactivity), increase of drug stability, and prolongation of duration in the body. The terminal modified polyoxyalkylene compounds include those having a carboxyl group, an aldehyde group, an amino group, a thiol group, a maleimido group, etc. as a terminal functional group capable of reacting with a side chain functional group of peptides or proteins, such as the amino group of a lysine residue, the carboxyl group of an aspartic acid or glutamic acid residue, the thiol group of a cysteine residue, or with the amino group or the carboxyl group of phospholipids or polymeric micelle starting materials.

In particular, modification of the side chain thiol group of a cysteine residue or a thiol group introduced into a lysine residue with a maleimido-terminated polyoxyalkylene compound forms a thioether linkage, which is firmer than other linkages formed by other modification methods. Conventional polyoxyalkylene compounds having a maleimido end group used for the modification have been prepared by allowing polyethylene glycol or methoxypolyethylene glycol to react with an ester of N-hydroxysuccinimide and 6-maleimidocaproic acid, etc. However, these polyoxyalkylene compounds contain an ester linkage between the polyoxyalkylene chain and a maleimido group and are therefore easily hydrolyzed in the living body.

α-Maleimidoethyloxy-ω-methoxy(polyoxyalkylene), which is described in WO92/16221, WO98/3887, JP-A-12-191700, Proc. Natl. Acad. Sci. U.S.A., 97 (15) (2000), pp. 8543–8553, and Biochem. J., 351 (1) (2000), pp. 87–93, similarly has low storage stability.

Terminal modified polyoxyalkylene compounds for medical application must have few impurities of higher molecular weight than the desired compound, and a high degree of active group substitution. Therefore, terminal modified polyoxyalkylene compounds with a high GPC purity and a high degree of substitution with a terminal active group.

Synthetic Communications, 22 (16) (1992), pp. 2425–2429 reports a process of producing a maleimido group-terminated polyoxyalkylene derivative having a $C_2$ alkyl group between the polyoxyalkylene chain and the maleimido group. The process reported cannot be seen as suited for industrial production because a large quantity of diethyl ether, which has a low ignition point, is used in purifying the intermediate.

SUMMARY OF THE INVENTION

An object of the present invention is to provide a polyoxyalkylene derivative which is highly pure, excellent in storage stability, and is useful to modify biological substances.

Another object of the present invention is to provide a process of producing a highly pure polyoxyalkylene derivative with safety.

The present invention provides a polyoxyalkylene derivative represented by formula (I):

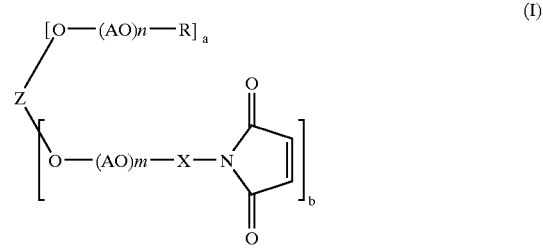

wherein Z represents a residue of a compound having 2 to 8 hydroxyl groups; AO represents an oxyalkylene group having 2 to 18 carbon atoms; n and m each represent an integer of 0 to 2000 provided that both n and m do not represent 0; a and b each represent an integer satisfying the relationships: $2 \leq a+b \leq 8$ and $1 \leq b$; R represents a hydrocarbon group having 1 to 30 carbon atoms; and X represents a divalent hydrocarbon group having 3 to 10 carbon atoms.

The polyoxyalkylene derivative according to the present invention preferably has a GPC purity of 90% or higher and a maleimido group substitution degree of 90% or higher.

The polyoxyalkylene derivative of the present invention preferably has a maleimido group substitution degree half-life time (50% reduction time) of 48 hours or longer in a hydrolysis stability test conducted at pH 7 and 23° C.

Of the polyoxyalkylene derivatives represented by formula (I), those in which Z is a residue of a compound having 3 to 8 hydroxyl groups, and a and b satisfy the relationship: $3 \leq a+b \leq 8$ and $1 \leq b$ are preferred.

The polyoxyalkylene derivative according to the invention is preferably used for modification of a biological substance.

Of the polyoxyalkylene derivatives represented by formula (I), those in which X is a divalent hydrocarbon group having 3 carbon atoms are preferred.

The present invention also provides a process for producing a polyoxyalkylene derivative represented by formula (I), which comprises allowing an amino-terminated polyoxyalkylene derivative represented by formula (III):

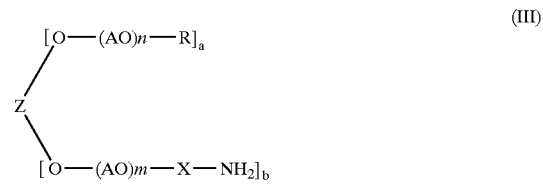

wherein Z, AO, n, m, a, b, R, and X are as defined above, to react with maleic anhydride to form a maleamic acid-terminated polyoxyalkylene derivative represented by formula (IV):

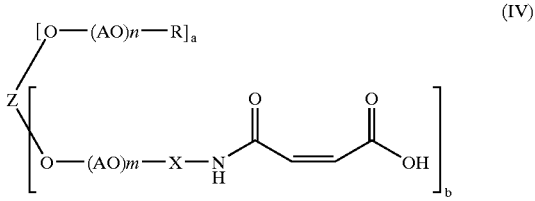

(IV)

wherein Z, AO, n, m, a, b, R, and X are as defined above, dissolving the compound represented by formula (IV) in 50 to 500 vol/wt %, based on the compound represented by formula (IV), of an organic solvent, crystallizing the compound represented by formula (IV) from 300 to 5000 vol/wt %, based on the compound represented by formula (IV), of a mixture of ethyl acetate and n-hexane, and imidizing the maleamic acid end group.

The amino-terminated polyoxyalkylene derivative represented by formula (III) is preferably prepared from a hydroxyl-terminated polyoxyalkylene derivative represented by formula (II):

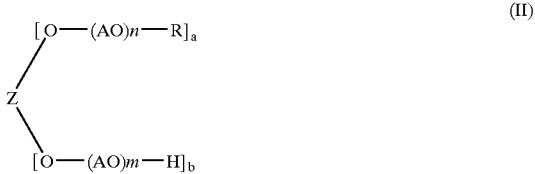

(II)

wherein Z, AO, n, m, a, b, and R are as defined above, through cyanation followed by hydrogenation.

The maleamic acid-terminated polyoxyalkylene derivative represented by formula (IV) obtained in the process of the invention preferably has a maleic anhydride content of 0.5 wt % or less.

DETAILED DESCRIPTION OF THE INVENTION

The polyoxyalkylene derivative according to the invention is specially useful to modify a biological substance. The term "biological substance" as used herein denotes substances necessary for maintaining vital activities in the living body and substances related thereto. Included under this term are physiologically active substances, structural proteins, and phospholipids. Further included are synthetically prepared poly(amino acid)s, such as polylysine and polyglutamic acid.

The physiologically active substances include peptides having a thiol group, such as glutathione; physiologically active proteins, such as hemoglobin and insulin; enzymes, such as lipase and protease; and peptides, proteins and enzymes obtained by chemical modification or gene recombination. The structural proteins include collagen and keratin which constitute living tissue.

The polyoxyalkylene derivative represented by formula (I) will be described in detail.

In formula (I), Z represents a residue of a compound having 2 to 8 hydroxyl groups, preferably 3 to 8 hydroxyl groups. The compound having 2 to 8 carbon atoms includes ethylene glycol, propylene glycol, butylene glycol, glycerol, diglycerol, triglycerol, tetraglycerol, pentaglycerol, hexaglycerol, and pentaerythritol. Preferred are ethylene glycol, glycerol, diglycerol, hexaglycerol, and pentaerythritol. Still preferred are glycerol, diglycerol, hexaglycerol, and pentaerythritol.

The oxyalkylene group having 2 to 18 carbon atoms which is represented by AO includes an oxyethylene group, an oxypropylene group, an oxybutylene group, an oxytetramethylene group, an oxystyrene group, an oxydodecylene group, an oxytetradecylene group, an oxyhexadecylene group, and an oxyoctadecylene group. Preferred are oxyalkylene groups having 2 to 4 carbon atoms, with an oxyethylene group being still preferred.

n and m each represent the number of moles of the added oxyalkylene group (AO), each ranging from 0 to 2000 provided that both n and m do not represent zero n and m each preferably ranges from 20 to 2,000, particularly 40 to 1,000. The sum of n and m preferably ranges from 20 to 1,200, particularly 40 to 400.

a and b each represent the number of the polyoxyalkylene chains, satisfying the relationships: $2 \leqq a+b \leqq 8$ and $1 \leqq b$, preferably $3 \leqq a+b \leqq 8$ and $1 \leqq b$. Incorporation of a biological substance into an immune system can be suppressed by modification, and modification of a physiologically active substance with a polyoxyalkylene derivative having two or more polyoxyalkylene chains produces a desired modification effect without impairing the physiological activity. Modification of a physiologically active substance with a polyoxyalkylene derivative having two or more maleimido end groups results in an increased molecular weight, which is more effective in suppressing incorporation into an immune system.

n, m, a, and b are indices decisive of the whole molecular weight of the polyoxyalkylene derivative. They satisfy the relationship: $1 \leqq (n \times a + m \times b) \leqq 16{,}000$, preferably $20 \leqq (n \times a + m \times b) \leqq 5{,}000$, still preferably $40 \leqq (n \times a + m \times b) \leqq 1{,}200$. With these relationships satisfied, the molecular weight of the polyoxyalkylene derivative of formula (I) falls within a range of 250 to 700,000, preferably 1000 to 200,000, still preferably 2000 to 50,000.

The hydrocarbon group having 1 to 30 carbon atoms as represented by R includes aliphatic hydrocarbon groups, e.g., methyl, ethyl, propyl, isopropyl, butyl, isobutyl, t-butyl, pentyl, isopentyl, hexyl, heptyl, 2-ethylhexyl, octyl, nonyl, decyl, undecyl, dodecyl, isotridecyl, tetradecyl, hexadecyl, isohexadecyl, octadecyl, isooctadecyl, octadecenyl, octyldodecyl, docosyl, and decyltetradecyl; and aromatic hydrocarbon groups, e.g., benzyl, cresyl, butylphenyl, dibutylphenyl, octylphenyl, dodecylphenyl, dioctylphenyl, dinonylphenyl, naphthyl, styrenated phenyl, p-methoxybenzyl, and triphenylmethyl. Preferred of them are methyl, ethyl, t-butyl, octadecyl, benzyl, p-methoxybenzyl, and triphenylmethyl. Methyl, t-butyl, and benzyl are still preferred.

The divalent hydrocarbon group having 3 to 10 carbon atoms as represented by X includes straight-chain or branched hydrocarbon groups, e.g., trimethylene, isopropylene, tetramethylene, isobutylene, dimethylmethylene, pentamethylene, hexamethylene, heptamethylene, octamethylene, nonamethylene, and decamethylene; and aromatic hydrocarbons, e.g., phenylmethylene. Preferred of them are trimethylene, tetramethylene, pentamethylene, hexamethylene, heptamethylene, octamethylene, nonamethylene, and decamethylene. Still preferred are trimethylene, hexamethylene, heptamethylene, octamethylene, nonamethylene, and decamethylene.

In carrying out cyanation of a compound having a hydroxyl group, cyanoethylation consisting of acrylonitrile addition is an excellent method in terms of purity and yield. A cyanoethylated compound is led to a compound with a divalent hydrocarbon group having 3 carbon atoms. From this viewpoint, the polyoxyalkylene derivative of formula (I) is preferably one in which X is a divalent hydrocarbon group having 3 carbon atoms.

On the other hand, the polyoxyalkylene derivative of formula (I) in which X is a divalent hydrocarbon group having 6 to 10 carbon atoms exhibits superiority in hydrolysis stability and is therefore preferred for assuring quality equivalence in the development of pharmaceutical preparations by modifying biological substances.

In application to pharmaceutical preparations, the polyoxyalkylene derivative is required to have high purity to meet the demand for preparation homogeneity and reactivity with biological substances. From the aspect of preparation homogeneity, the polyoxyalkylene derivative is particularly required to have a high GPC purity, which is a chromatographic purity relating to contents of compounds whose molecular weights are double, triple, etc. what is intended.

It is preferred for the polyoxyalkylene derivative according to the present invention to have a GPC purity of at least 90%, particularly 95% or higher.

A GPC purity is measured by gel-permeation chromatography (GPC) under the following conditions.

Columns: A series of three columns SHODEX KF804L (inner diameter; 8 mm; height; 30 cm; available from Showa Denko K.K.)
Eluent: Tetrahydrofuran
Flow rate: 1.0 ml/min
Column temperature: 40° C.
Detector: Differential refractometer
Sample: 0.1 wt % tetrahydrofuran solution
Loading: 100 µl Where a peak is separated, it is vertically divided at the minimum between the apices. Where a peak has a shoulder, it is vertically divided at the inflection point. The area ratio of the main peak is calculated from the areas of the divided peaks.

In order to assure sufficient reactivity with a biological substance, it is preferred for the polyoxyalkylene derivative to have a high degree of substitution with a maleimido group, the active end group. At a low degree of substitution with the active end group, the production ratio of a desired modified biological substance will be reduced, which leads to reduction of performance of the preparation, such as reduction in duration in blood. The polyoxyalkylene derivative used to modify a biological substance preferably has a 90% or higher, particularly 92% or higher, degree of substitution with maleimido group, the functional end group.

The maleimido group substitution degree is measured by $^1$H-NMR analysis at 400 MHz with ECP400, supplied by JEOL Ltd., on a sample weighing between 15 and 20 mg dissolved in 0.55 ml deuteric chloroform. The integral of each of the peak assigned to maleimido groups (δ 6.69, s), the peak assigned to the raw material (maleamic acid-terminated polyoxyalkylene derivative) (δ 6.35, dd), and the peak assigned to the reaction intermediate (δ 7.22 and 6.62, d) is obtained from the NMR spectrum. The percentage of the peak area assigned to maleimido groups to the total of the integrals is taken as a maleimido group substitution degree.

The reaction with a biological substance is usually carried out in a buffer solution. Therefore the polyoxyalkylene derivative is required to have excellent stability against hydrolysis in a buffer solution. If not, the polyoxyalkylene derivative will undergo hydrolysis in a buffer solution only to attain a low degree of modification of the biological substance, failing to produce sufficient modification effects. In such a case, the polyoxyalkylene derivative would have to be used in a large excess to achieve sufficient modification effects.

The hydrolysis stability of the polyoxyalkylene derivative used to modify a biological substance is such that the half-life time (50% reduction time) of the maleimido group substitution degree in a hydrolysis stability test at pH 7 and 23° C. is 48 hours or longer, preferably 54 hours or longer, still preferably 60 hours or longer. It is also preferred for the polyalkylene derivative to have a 25% reduction time of 24 hours or longer and a 70% reduction time of 67 hours or longer, preferably a 25% reduction time of 27 hours or longer and a 70% reduction time of 75 hours or longer, in the hydrolysis stability test.

The hydrolysis stability test is performed as follows. A sample compound weighing 0.02 g is dissolved in 20 ml of a 50 mM phosphoric acid buffer (pH 7) in a 50 ml screw bottle glass and allowed to stand at 23° C. A 4 ml aliquot harvested after 24 hours, 48 hours or 72 hours from the dissolving is mixed with a few drops of a 1% phosphoric acid aqueous solution and lyophilized. The solid is dissolved in chloroform, and insoluble matter is removed by filtration. The filtrate is concentrated in an evaporator to prepare a sample, which is analyzed by $^1$H-NMR to determine the maleimido group substitution degree. The maleimido group substitution degree at each time of measurement is divided by the initial maleimido group substitution degree, and the quotient is multiplied by 100 to give a residual ratio (%) of the maleimido groups. The time at which the residual ratio is 75%, 50% (half), and 30% is taken as a 25% reduction time, a 50% reduction time (half-life time), and 70% reduction time, respectively. The 25% reduction time, 50% reduction time (half-life time), and 70% reduction time are obtainable by plotting the residual ratios after 24, 48, and 72 hours on the ordinate with time as abscissa, obtaining a regression line with the intercept as 100, and calculating the times at which the residual ratio is 75%, 50% and 30% based on the regression.

The polyoxyalkylene derivative according to the present invention can be prepared from an amino-terminated polyoxyalkylene derivative represented by formula (III). From the viewpoint of purity, the process preferably starts with a hydroxyl-terminated polyoxyalkylene derivative represented by formula (II). The process is illustrated by the following scheme:

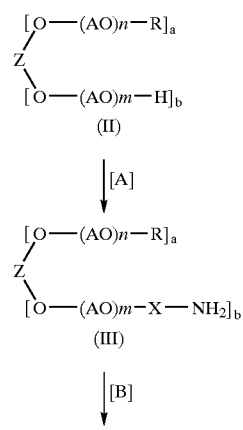

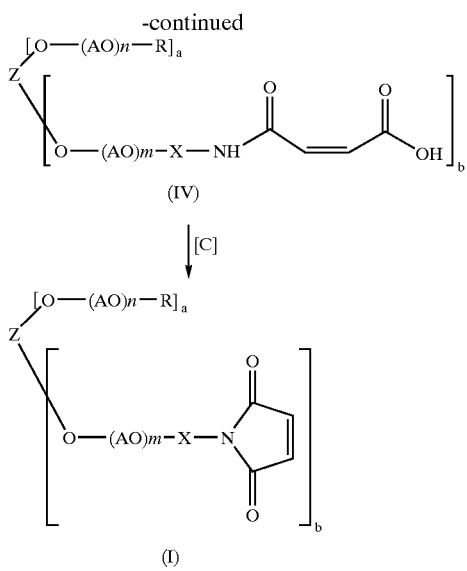

Step [A] consists of cyanation of the hydroxyl-terminated polyoxyalkylene derivative (II) in the presence of an alkali catalyst and subsequent hydrogenation to form an amino-terminated polyoxyalkylene derivative (III). The cyanation is achieved by addition of, for example, acrylonitrile or a halide of a nitrile group-containing divalent hydrocarbon having 3 to 10 carbon atoms. Hydrogenation of the resulting cyanide compound gives the compound (III) having a divalent hydrocarbon group containing 3 to 10 carbon atoms between the polyoxyalkylene chain and the amino end group. The halide as a cyanating agent is preferably a bromide, a chloride or an iodide, still preferably a chloride or a bromide.

The cyanation is preferably conducted in water or an organic solvent capable of dissolving the starting compound (II). Suitable organic solvents include chloroform, toluene, acetonitrile, and dimethylformamide, with toluene and acetonitrile being preferred. The solvent is used in an amount of 50 to 500 vol/wt %, preferably 70 to 300 vol/wt %, based on the compound (II).

The alkali catalyst which can be used for cyanation includes strong alkali metal hydroxides, such as potassium hydroxide and sodium hydroxide, and strong alkali alcoholates, such as sodium methylate. The catalyst is used in an amount of 0.5 to 25 wt %, preferably 3 to 10 wt %, based on the compound (II).

The cyanating agent, such as acrylonitrile, is preferably used in an amount of 1 to 100 equivalents, particularly 10 to 60 equivalents, per hydroxyl equivalent of the compound (II).

The cyanation reaction is preferably carried out at a temperature of −20° to 150° C., particularly 0 to 100° C., for a period of 1 to 10 hours, particularly 2 to 6 hour. After the reaction, the catalyst is removed by washing with water or adsorption treatment, and the solvent is removed to give a polyoxyalkylene cyanide.

The resulting cyanide compound is then hydrogenated in the presence of a catalyst commonly employed for hydrogenation to yield the amino-terminated polyoxyalkylene derivative (III). The hydrogenation reaction is preferably carried out in an organic solvent capable of dissolving the cyanide, such as toluene or ethanol. Toluene is particularly preferred; The solvent is used in an amount of 50 to 500 vol/wt %, preferably 70 to 300 vol/wt %, based on the polyoxyalkylene cyanide.

Suitable catalysts for hydrogenation include nickel and cobalt, with nickel being preferred. The catalyst is preferably used in an amount of 0.5 to 25 wt %, particularly 1 to 10 wt %, based on the polyoxyalkylene cyanide. In using a nickel catalyst, it is advisable to add ammonia gas to prevent undesirable side reaction during hydrogenation. Ammonia gas is preferably added in an amount of 5 to 30 wt %, particularly 10 to 20 wt %, based on the polyoxyalkylene cyanide.

The hydrogenation reaction is preferably performed at a hydrogen pressure of 1 to 10 MPa, particularly 3 to 6 MPa, at a temperature of 80 to 200° C., particularly 100 to 150° C., for a period of 0.5 to 10 hours, particularly 1 to 5 hours. After the reaction, the catalyst is removed by filtration, and the solvent is removed to give the amino-terminated polyoxyalkylene derivative (III).

If desired, the polyoxyalkylene cyanide and the compound (III) prepared in step [A] may be purified by crystallization, adsorption or like procedures.

Step [B] consists of allowing the compound (III) prepared in step [A] to react with maleic anhydride to obtain a maleamic acid-terminated polyoxyalkylene of formula (IV).

The amine purity of the amino-terminated polyoxyalkylene derivative (III) is desirably 90% or higher, more desirably 95% or higher. If the amine purity is low, cyclization in step [C] does not take place sufficiently, resulting in a low maleimido group substitution degree of the final product, the polyoxyalkylene derivative of formula (I).

The amine purity can be determined by liquid chromatography under the following conditions.

Column: TSKgel SP-5PW (inner diameter: 7.5 mm; length; 7.5 cm, available from Tosoh Corp.)
Eluent: 2 mM phosphoric acid buffer (pH 6.5)
Flow rate: 0.5 ml/min
Column temperature: 40° C.
Detector: Differential refractometer
Sample: 0.5 wt % solution in 2 nm phosphoric acid buffer (pH 6.5)
Loading: 20 µl Where a peak is separated, it is vertically divided at the minimum between the apices where a peak has a shoulder, it is vertically divided at the inflection point. The area ratio of the main peak is calculated from the areas of the divided peaks.

In carrying out the reaction, the compound (III) is preferably dissolved in an organic solvent capable of dissolving the compound (III), preferably chloroform or toluene. The solvent is used in an amount of 50 to 500 vol/wt %, preferably 70 to 300 vol/wt %, based on the compound (III). Maleic anhydride is preferably used in an amount of 1.0 to 20 equivalents, particularly 5 to 15 equivalents, per amino equivalent of the compound (III). The reaction temperature is preferably 20 to 80° C., still preferably 40 to 60° C. The reaction time is preferably 0.5 to 10 hours, particularly 1 to 5 hours.

The resulting maleamic acid-terminated polyoxyalkylene derivative (IV) is dissolved in an organic solvent capable of dissolving the compound (IV) and crystallized by using a mixture of ethyl acetate and n-hexane.

The organic solvent for the compound (IV) preferably includes chloroform, toluene, acetonitrile, and dimethylformamide, with chloroform and toluene being particularly preferred. The organic solvent is used in an amount of 50 to 500 vol/wt %, preferably 70 to 300 vol/wt %, based on the compound (IV).

The ethyl acetate/n-hexane mixed solvent is used in an amount of 300 to 5000 vol/wt %, preferably 500 to 2000 vol/wt %, based on the compound (IV). The ethyl acetate to n-hexane mixing ratio is 1:9 to 9:1, preferably 4:6 to 6:4, by volume.

In the crystallization step, the temperature where the compound (IV) is dissolved with the organic solvent is preferably 0 to 80° C., still preferably 20 to 40° C. The temperature where the ethyl acetate/n-hexane mixture is added to this solution in which the compound (IV) is dissolved in the organic solvent so as to crystallize is preferably 20 to 35° C. Ethyl acetate and n-hexane may be added separately. Crystallization may be carried out repeatedly.

It is desirable for the resulting maleamic acid-terminated polyoxyalkylene derivative (IV) to have a maleic anhydride content of 0.5 wt % or less, particularly 0.1 wt % or less. A high maleic anhydride content in the compound (IV) can result in formation of impurities having higher molecular weights than an intended molecular weight, which will result in a reduced GPC purity.

The maleic anhydride content can be determined by $^1$H-NMR analysis at 400 MHz with ECP400, supplied by JEOL Ltd., on a solution of 15 to 20 mg of a sample compound in 0.55 ml of deuteric chloroform. The integral of the peak assigned to maleic anhydride ($\delta$ 7.05, s, 2H) is obtained from the resulting NMR spectrum as compared with a standard peak (for example, a peak assigned to a methoxy group as a standard; $\delta$ 3.38, s, 3H), from which the maleic anhydride content is calculated according to equation:

Maleic anhydride content (wt %)=[(integral/2)×98/molecular weight of maleamic acid-terminated polyoxyalkylene)×100

Step [C] consists of cyclization (imidation) of the terminal maleamic acid of the compound (IV) to give the polyoxyalkylene derivative (I).

The cyclization reaction is carried out by dissolving the compound (IV) in 5 to 1000 wt %, preferably 100 to 500 wt %, based on the compound (IV), of acetic anhydride, adding thereto 1 to 50 wt %, preferably 5 to 40 wt %, based on the compound (IV), of a catalyst, such as sodium acetate or triethylamine, and heating the reaction system at 60 to 130° C. If desired, an organic solvent can be used. Useful organic solvents include chloroform, acetonitrile, and toluene. The organic solvent is used in an amount of 50 to 500 vol/wt %, preferably 70 to 300 vol/wt %, based on the compound (IV).

After the reaction, the catalyst is removed by filtration, and the filtrate is concentrated at 60 to 130° C. under reduced pressure. The concentrate is dissolved in an organic solvent, and an ethyl acetate/n-hexane mixture is added to the solution to crystallize. The crystals are collected by filtration and dried to yield the desired compound (I).

The organic solvent preferably includes chloroform and toluene. The organic solvent is used in an amount of 50 to 500 vol/wt %, preferably 70 to 300 vol/wt %, based on the compound (I).

The ethyl acetate/n-hexane mixed solvent is used in an amount of 300 to 5000 vol/wt %, preferably 500 to 2000 vol/wt %, based on the compound (I). The ethyl acetate to n-hexane mixing ratio is 1:9 to 9:1, preferably 4:6 to 6:4, by volume. Ethyl acetate and n-hexane may be added separately. The crystallization may be conducted repeatedly.

Modification of a biological substance with the polyoxyalkylene derivative of the invention can be achieved the following method. For example, a biological substance is dissolved in a phosphoric acid buffer and cooled to 10° C. or lower. The maleimido-terminated polyoxyalkylene derivative is added to the cooled solution, followed by stirring for 1 to 10 hours. The reaction system is desalted and lyophilized to give a polyoxyalkylene derivative-modified biological substance.

The polyoxyalkylene derivative of the invention is highly pure and excellent in storage stability owing to the stability of its maleimido moiety. Therefore, when it is used to modify a biological substance, the resulting polyoxyalkylene derivative-modified biological substance also exhibits excellent stability. The process according to the invention yields a desired high purity polyoxyalkylene derivative with safety. The modified substance where the biological substance is modified by using the polyoxyalkylene derivative of the invention is excellent in stability and useful.

The present invention will now be illustrated in greater detail with reference to Examples.

EXAMPLE 1

Cyanation:

In a 3 liter four-necked flask equipped with a stirrer, a dropping funnel, a thermometer, and a nitrogen-bubbling tube was put 640 g of methoxypolyoxyethylene of formula (II) in which n+m=112, a=1, and b=1 (MEH-50H, available from NOF Corp.), and 640 g of ion-exchanged water was added to dissolve the compound. The solution was cooled to 10° C. or lower, and 40 g of 50% potassium hydroxide was added thereto. The solution was further cooled to 5° C. or lower, and 340 g of acrylonitrile was added thereto dropwise over 2 hours while keeping the liquid temperature to 5° C. or lower. After the addition, the stirring was continued for an additional 2 hour period. After completion of the reaction, the reaction mixture was neutralized by addition of 24 g of 85% phosphoric acid. To 842 g of the reaction mixture was added a solution of 500 g of sodium chloride in 2800 g of ion-exchanged water, and the mixture was extracted with 1000 ml of chloroform. The chloroform layer was separated, and the aqueous layer was again extracted with 500 ml of chloroform. The combined chloroform extract was filtered, removed the solvent at 90° C. under reduced pressure of 0.3 kPa to give 640 g of crude cyanoethylated methoxypolyoxyethylene.

In a 10 liter beaker equipped with a stirrer and a nitrogen seal tube was put 600 g of the crude cyanoethylated methoxypolyoxyethylene and dissolved in 500 ml of chloroform. A mixture of 4 L of ethyl acetate and 4 L of n-hexane was poured into the solution, followed by stirring for 30 minutes to crystallize. The crystals were collected by filtration crystallization was repeated by using 400 ml of chloroform and another mixture of ethyl acetate (4 L) and n-hexane (4 L). The resulting crystals were dried to give 540 g of cyanoethylated methoxypolyoxyethylene.

Amination:

In a 1 liter autoclave equipped with a stirrer, a thermometer, a nitrogen-introducing tube, a hydrogen-introducing tube, and an ammonia-introducing tube were put 200 g of the cyanoethylated methoxypolyoxyethylene, 400 g of toluene, and 4 g of a nickel catalyst. After the autoclave was purged with nitrogen, the mixture was heated to 60° C. to dissolve the compound. Into the solution was introduced 30 g of ammonia gas, and hydrogen gas was then introduced to 4 MPa. The temperature of the autoclave was raised to 130° C., and the mixture was stirred for 3 hours. After the autoclave was cooled to 80° C., the catalyst was removed by filtration, and the filtrate was removed the solvent at 90° C. under reduced pressure of 0.3 kPa for 1 hour to give 170 g of methoxypolyoxyethylene propylamine, which was found to have an amine purity of 95.2%.

Maleimidation:

Into a 1 liter four-necked flask equipped with a stirrer, a thermometer, a condenser, and a nitrogen-bubbling tube were charged 164 g of the methoxypolyoxyethylene propylamine and 325 ml of toluene and heated to 50° C. to prepare a solution. To the solution was added 32 g of maleic anhydride, followed by stirring for 4 hours. The reaction mixture was cooled to 40° C., and a mixture of 800 ml of ethyl acetate and 800 ml of hexane was poured therein, followed by stirring for 30 minutes to crystallize. The crystals collected by filtration were again dissolved in 325 ml of toluene, and a mixture of 800 ml of ethyl acetate and 800 ml of hexane was poured therein, followed by stirring for 30 minutes to crystallize. The crystals collected by filtration were dried to give 167 g of methoxypolyoxyethylene propylmaleamic acid, which was found to have a maleic anhydride content of 0.0011 wt %.

Into a 1 liter four-necked flask equipped with a stirrer, a thermometer, a condenser, and a nitrogen-bubbling tube were charged 167 g of the resulting methoxypolyoxyethylene propylmaleamic acid, 500 ml of acetic anhydride, and 64 g of sodium acetate. The mixture was heated to 90° C., at which it was stirred for 3 hours to conduct reaction. After cooling to 50° C., the reaction mixture was filtered to remove sodium acetate, and the filtrate was concentrated at 90° C. under reduced pressure of 0.3 kPa. The concentrate was dissolved in 330 ml of chloroform, and any insoluble matter was removed by filtration. A mixture of 1 liter of ethyl acetate and 1 liter of hexane was poured into the filtrate, followed by stirring for 30 minutes to crystallize. The crystals were collected by filtration. The crystals were again dissolved in 330 ml of chloroform and crystallized from another mixture of ethyl acetate (1 liter) and hexane (1 liter) by stirring for 30 minutes. The crystals collected by filtration were dried to afford 160 g of methoxypolyoxyethylene propylmaleimide, which was a pale pink.

EXAMPLE 2

Cyanation:

In a 5 liter four-necked flask equipped with a stirrer, a dropping funnel, a thermometer, and a nitrogen-bubbling tube was put 1600 g of polyethylene glycol of formula (II) in which a=0, m=113, and b=2 (PEG 11000, available from NOF Corp.; molecular weight: 10000), and 1600 g of ion-exchanged water was added to dissolve the compound. The solution was cooled to 10° C. or lower, and 100 g of 50% potassium hydroxide was added thereto. The solution was further cooled to 5° C. or lower, and 850 g of acrylonitrile was added thereto dropwise over 2 hours while keeping the liquid temperature at 5° C. or lower. After the addition, the stirring was continued for an additional 2 hour period. After completion of the reaction, the reaction mixture was neutralized by addition of 60 g of 85% phosphoric acid. The reaction mixture was worked up in the same manner as in Example 1 by using a solution of 1250 g of sodium chloride in 7000 g of ion-exchanged water, 2500 ml of chloroform, and 1250 ml of chloroform to obtain 1600 g of crude dicyanoethylated polyoxyethylene.

In a 30 liter beaker equipped with a stirrer and a nitrogen seal tube was put the crude dicyanoethylated polyoxyethylene (1600 g) and dissolved in 1.4 liter of chloroform. A mixture of 11.1 liters of ethyl acetate and 11.1 liters of hexane was poured into the solution, followed by stirring for 30 minutes to crystallize. The crystals were collected by filtration. The crystals were again dissolved in 1.4 liter of chloroform, and another mixture of ethyl acetate (11.1 liters) and n-hexane (11.1 liters) was poured therein, followed by stirring. The crystals thus precipitated were collected by filtration and dried to give 1400 g of dicyanoethylated polyoxyethylene.

Amination:

In a 1 liter autoclave equipped with a stirrer, a thermometer, a nitrogen-introducing tube, a hydrogen-introducing tube, and an ammonia-introducing tube were put 200 g of the dicyanoethylated polyoxyethylene, 400 g of toluene, and 9 g of a nickel catalyst. The mixture was allowed to react and worked up in the same manner as in Example 1 to give 170 g of polyoxyethylene dipropylamine, which was found to have an amine purity of 93.7%.

Maleimidation:

Into a 1 liter four-necked flask equipped with a stirrer, a thermometer, a condenser, and a nitrogen-bubbling tube were charged 164 g of the polyoxyethylene dipropylamine and 325 ml of toluene and heated to 50° C. to prepare a solution. To the solution was added 32 g of maleic anhydride, followed by stirring for 4 hours. The reaction mixture was cooled to 40° C., and a mixture of 800 ml of ethyl acetate and 800 ml of hexane was poured therein, followed by stirring for 30 minutes to crystallize. The crystals collected by filtration were again dissolved in 325 ml of toluene, a mixture of 800 ml of ethyl acetate and 800 ml of hexane was poured therein, followed by stirring for 30 minutes to crystallize. The crystals collected by filtration were dried to give 165 g of polyoxyethylene dipropylmaleamic acid, which was found to have a maleic anhydride content of 0.0018 wt %.

Into a 1 liter four-necked flask equipped with a stirrer, a thermometer, a condenser, and a nitrogen-bubbling tube were charged 165 g of the resulting polyoxyethylene dipropylmaleamic acid, 500 ml of acetic anhydride, and 63 g of sodium acetate. The mixture was heated to 90° C., at which it was stirred for 3 hours to conduct reaction. After cooling to 50° C., the reaction mixture was filtered to remove sodium acetate, and the filtrate was concentrated at 90° C. under reduced pressure of 0.3 kPa. The concentrate was dissolved in 360 ml of chloroform, and any insoluble matter was removed by filtration. A mixture of 1 liter of ethyl acetate and 1 liter of hexane was poured into the filtrate, followed by stirring for 30 minutes to crystallize. The crystals were collected by filtration. The crystals were again dissolved in 360 ml of chloroform and crystallized from a mixture of ethyl acetate (1 liter) and hexane (1 liter) by stirring for 30 minutes. The crystals collected by filtration were dried to furnish 160 g of polyoxyethylene dipropylmaleimide, which was a pale pink.

EXAMPLE 3

Cyanation:

In a 5 liter four-necked flask equipped with a stirrer, a dropping funnel, a thermometer, and a nitrogen-bubbling tube was put 1600 g of tetra(polyoxyethylene) diglycerol ether of formula (II) in which a=0, m=56, and b=4 (DGE-10000, available from NOF Corp.; molecular weight: 10000), and 1600 g of ion-exchanged water was added to dissolve the compound. The solution was cooled to 10° C. or lower, and 100 g of 50% potassium hydroxide was added thereto. The solution was further cooled to 5° C. or lower, and 850 g of acrylonitrile was added thereto dropwise over 2 hours while keeping the liquid temperature at 5° C. or lower. After the addition, the stirring was continued for an additional 2 hour period. After completion of the reaction, the reaction mixture was neutralized by addition of 60 g of 85% phosphoric acid. The reaction mixture was worked up in the same manner as in Example 1 by using a solution of 1250 g of sodium chloride in 7000 g of ion exchanged water, 2500 ml of chloroform, and 1250 ml of chloroform to give 1600 g of crude tetracyanoethylated tetra (polyoxyethylene) diglycerol.

In a 30 liter beaker equipped with a stirrer and a nitrogen seal tube was put the crude tetracyanoethylated tetra (polyoxyethylene) diglycerol (1600 g) and dissolved in 1.4 liter of chloroform. A mixture of 11.1 liters of ethyl acetate and 11.1 liters of hexane was poured into the solution, followed by stirring for 30 minutes to crystallize. The crystals were collected by filtration. The crystals were again dissolved in 1.4 liter of chloroform, and another mixture of ethylacetate (11.1 liter) and n-hexane (11.1 liter) was poured therein, followed by stirring for 30 minutes to crystallize. The resulting crystals collected by filtration were dried to yield 1400 g of tetracyanoethylated tetra(polyoxyethylene) diglycerol.

Amination:

In a 1 liter autoclave equipped with a stirrer, a thermometer, a nitrogen-introducing tube, a hydrogen-introducing tube, and an ammonia-introducing tube were put 200 g of the tetracyanoethylated tetra(polyoxyethylene) diglycerol, 400 g of toluene, and 9 g of a nickel catalyst. The mixture was allowed to react and worked up in the same manner as in Example 1 to give 170 g of tetra (polyoxyethylene) diglycerol tetrapropylamine, which was found to have an amine purity of 93.1%.

Maleimidation:

Into a 1 liter four-necked flask equipped with a stirrer, a thermometer, a condenser, and a nitrogen-bubbling tube were charged 164 g of the tetra(polyoxyethylene) diglycerol tetrapropylamine and 325 ml of toluene and heated to 50° C. to prepare a solution. To the solution was added 64 g of maleic anhydride, followed by stirring for 4 hours. The reaction mixture was cooled to 40° C., and a mixture of 800 ml of ethyl acetate and 800 ml of hexane was poured therein, followed by stirring for 30 minutes to crystallize. The crystals collected by filtration were again dissolved in 325 ml of toluene, a mixture of 800 ml of ethyl acetate and 800 ml of hexane was poured therein, and the mixture was stirred for 30 minutes to crystallize. The crystals collected by filtration were dried to give 167 g of tetra(polyoxyethylene) diglycerol tetrapropylmaleamic acid, which was found to have a maleic anhydride content of 0.025 wt %.

Into a 1 liter four-necked flask equipped with a stirrer, a thermometer, a condenser, and a nitrogen-bubbling tube were charged 167 g of the resulting tetra(polyoxyethylene) diglycerol tetrapropylmaleamic acid, 500 ml of acetic anhydride, and 63 g of sodium acetate. The mixture was heated to 90° C., at which it was stirred for 3 hours to conduct reaction. After cooling to 50° C., the reaction mixture was filtered to remove sodium acetate, and the filtrate was concentrated at 90° C. under reduced pressure of 0.3 kPa. The concentrate was dissolved in 360 ml of chloroform, and any insoluble matter was removed by filtration. A mixture of 1 liter of ethyl acetate and 1 liter of hexane was poured into the filtrate, followed by stirring for 30 minutes to crystallize. The crystals were collected by filtration. The crystals were again dissolved in 360 ml of chloroform and crystallized from a mixture of ethyl acetate (1 liter) and hexane (1 liter) by stirring for 30 minutes. The crystals collected by filtration were dried to afford 162 g of tetra(polyoxyethylene) diglycerol tetrapropylmaleimide, which was a pale pink.

COMPARATIVE EXAMPLE 1

Methoxypolyoxyethylene ethylmaleimide was synthesized from methoxypolyoxyethylene propylamine (molecular weight: 5000) by the method described in the literature (*Synthetic Communications,* 22 (16) (1992), pp. 2425–2429).

The starting methoxypolyoxyethylene propylamine was prepared by cyanation and amination using the same materials and the same method as in Example 1. The resulting methoxypolyoxyethylene propylamine had an amine purity of 96.8%.

Into a 50 ml flask were charged 2.5 g of the methoxypolyoxyethylene propylamine, 460 mg of maleic anhydride, and 10 ml of dioxane and allowed to react by stirring at 80° C. for 30 minutes. After cooling, 500 ml of diethyl ether was poured into the reaction mixture, and the mixture was allowed to stand overnight to crystallize. The crystals were collected by filtration, washed with diethyl ether, and dried in vacuo to give methoxypolyoxyethylene propylmaleamic acid, which was found to have a maleic anhydride content of 0.086 wt %.

In a 50 ml flask were put the resulting methoxypolyoxyethylene propylmaleamic acid, 20 ml of acetic anhydride, and 1.0 g of sodium acetate, and the mixture was stirred at 100° C. for 45 minutes to conduct reaction. After cooling, the reaction mixture was evaporated to remove the solvent. The residue was dissolved in 50 ml of dichloromethane and treated by activated carbon, which was removed afterward by filtration. To the filtrate was added 500 ml of diethyl ether, and the system was allowed to stand overnight. The precipitated crystals were collected by filtration, washed with diethyl ether, and dried in vacuo to yield 2.2 g of methoxypolyoxyethylene propylmaleimide, which was a pale pink.

COMPARATIVE EXAMPLE 2

Methoxypolyoxyethylene propylamine was prepared by cyanation and amination using the same materials and the same method as used in Example 1. The resulting methoxypolyoxyethylene propylamine had an amine purity of 98.8%.

In a 1 liter four-necked flask equipped with a stirrer, a thermometer, a condenser, and a nitrogen-bubbling tube were put 164 g of the methoxypolyoxyethylene propylamine and 325 ml of toluene, followed by heating to 50° C. to prepare a solution. To the solution was added 32 g of maleic anhydride, and the mixture was stirred for 4 hours to conduct reaction. After completion of the reaction, an aliquot of the reaction mixture was analyzed to find the maleic anhydride content to be 15 wt %. To the reaction mixture were added 500 ml of acetic anhydride and 64 g of sodium acetate, and the mixture was heated up to 90° C. The reaction mixture was worked up in the same manner as in Example 1 to yield 164 g of methoxypolyoxyethylene propylmaleimide crystals, which were a deep brown.

COMPARATIVE EXAMPLE 3

Commercially available methoxypolyethylene glycol maleimide (Methoxypolyethylene glycol 5,000 maleimide, Product No. 63187, available from Fluka; molecular weight: 5000) was analyzed as Comparative Example 3.

The polyoxyalkylene derivatives of Examples 1 to 3 and Comparative Examples 1 to 3 were analyzed for GPC purity and maleimido group substitution degree. The results are shown in Table 1 below.

TABLE 1

| | GPC Purity (%) | Maleimido Group Substitution Degree (%) | Maleic Anhydride Content (wt %) |
|---|---|---|---|
| Example 1 | 97.7 | 95.7 | 0.0011 |
| Example 2 | 94.4 | 93.1 | 0.0018 |
| Example 3 | 92.8 | 92.2 | 0.025 |
| Compara. Example 1 | 99.2 | 84.7 | 0.086 |
| Compara. Example 2 | 51.6 | 94.3 | 15 |
| Compara. Example 3 | 98.4 | 78.0 | — |

It is seen that the polyoxyalkylene derivatives obtained by the process of the present invention exhibit a high GPC purity and a high maleimido group substitution degree, whereas those of Comparative Examples, which are out of the scope of the present invention, are unsatisfactory in both the attributes.

The polyoxyalkylene derivatives prepared in Example 1 and Comparative Example 3 were tested for hydrolysis stability and stability of lysozyme modified therewith according to the following test methods.

1) Hydrolysis Stability

A sample weighing 0.1 g was put in a 50 ml screw bottle glass and dissolved in 100 ml of a 50 mM phosphoric acid buffer adjusted to pH 7, and the solution was allowed to stand at 23° C. A 4 ml aliquot harvested after 24 hour, 48 hour or 72 hour standing was mixed with a few drops of a 1% phosphoric acid aqueous solution and lyophilized. The solid was dissolved in chloroform, and insoluble matter was removed by filtration. The filtrate was concentrated in an evaporator to prepare a sample, which was analyzed by $^1$H-NMR to determine the maleimido group substitution degree. The residual ratio (%) of the maleimido group substitution degree at each time of measurement compared with the initial value was as shown in Table 2.

TABLE 2

Residual ratio of Maleimido Substitution Degree

| | After 24 hrs (%) | After 48 hrs (%) | After 72 hrs (%) |
|---|---|---|---|
| Example 1 | 81.8 | 63.2 | 47.4 |
| Compara. Example 3 | 73.4 | 42.7 | 26.0 |

The 50% reduction time (half-life time), 25% reduction time, and 70% reduction time, as calculated from these results, of Example 1 were 67 hours, 33 hours, and 94 hours, respectively; and those of Comparative Example 1 were 46 hours, 23 hours, and 64 hours, respectively.

2) Stability of Modified Lysozyme

Chick egg white lysozyme was dissolved in a phosphoric acid buffer (pH 7.4) to prepare a 0.5 mM solution, which was cooled to 4° C. To the solution was added 2.5 times as much molar quantity of 2-iminothiolane hydrochloride (from Aldrich Chemical Co.) as the lysozyme, and the system was stirred overnight to convert the side chain amino group of the lysine residue into a thiol group. To the reaction mixture was then added twice molar-excess of maleimido-terminated polyoxyalkylene derivative of Example 1 or Comparative Example 3 as the lysozyme, and the system was allowed to react for 3 hours while cooling. After desalting inorganic salts, the filtrate was lyophilized to obtain polyoxyalkylene derivative-modified lysozyme.

A 0.1 g aliquot was weighed out of the modified lysozyme and dissolved in 20 ml of a 10 mM phosphoric acid buffer (pH 7.0; containing 0.1% methyl 4-hydroxybenzoate), and the solution was preserved at 40° C. The activity of the modified lysozyme was determined as follows after a prescribed time of preservation.

An adequate amount of dry microbial cells of *Micrococcus lysodeikticus* was mixed with 75 mM sodium phosphate (pH 6.2) by shaking to prepare a substrate solution having a concentration adjusted to give an absorbance of 1.00 at 640 nm with a 75 mM sodium phosphate aqueous solution as a control. The modified lysozyme was dissolved in purified water to prepare a sample solution containing 5 to 15 μg/g of the lysozyme.

To 3.0 ml of the substrate solution kept at 37° C. was added 0.1 ml of the sample solution. After stirring, the absorbance at 640 nm was measured with a 75 mM sodium phosphate aqueous solution as a control. The initial lysozyme activity being taken as 100, the activity residual ratio (%) after a prescribed time was calculated from the absorbance. The results are shown in Table 3 below.

TABLE 3

| | After 1 mth (%) | After 2 mths (%) | After 3 mths (%) | After 4 mths (%) |
|---|---|---|---|---|
| Example 1 | 98 | 91 | 85 | 78 |
| Compara. Example 3 | 80 | 64 | 46 | 31 |

The results shown in Table 2 and 3 prove that the polyoxyalkylene derivative of Comparative Example 3 which has a $C_2$ alkyl group between the polyoxyalkylene chain and the maleimido end group is inferior to the compound of Example 1 in stability before and after modifying an enzyme.

This application is based on Japanese patent application JP 2001-231045, filed Jul. 31, 2001, the entire content of which is hereby incorporated by reference, the same as if set forth at length.

What is claimed is:

1. A polyoxyalkylene derivative represented by formula (I):

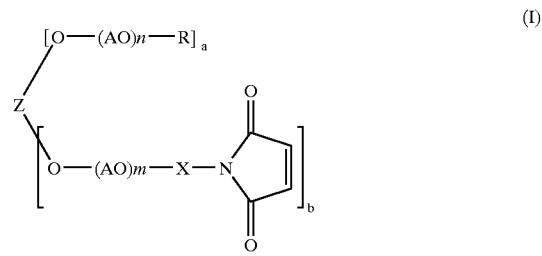

wherein Z represents a residue of a compound having 2 to 8 hydroxyl groups; AO represents an oxyalkylene group having 2 to 18 carbon atoms; n and m each represent an integer of 0 to 2000 provided that both n and m do not represent 0; a and b each represent an integer satisfying the relationships: $2 \leq a+b \leq 8$ and $1 \leq b$; R represents a hydrocarbon group having 1 to 30 carbon atoms; and X represents a divalent hydrocarbon group having 3 to 10 carbon atoms.

2. A polyoxyalkylene derivative according to claim 1, which has a GPC purity of 90% or higher and a maleimido group substitution degree of 90% or higher.

3. A polyoxyalkylene derivative according to claim 1, which has a maleimido group substitution degree half-life time (50% reduction time) of 48 hours or longer in a hydrolysis stability test conducted at pH 7 and 23° C.

4. A polyoxyalkylene derivative according to claim 2, which has a maleimido group substitution degree half-life time (50% reduction time) of 48 hours or longer in a hydrolysis stability test conducted at pH 7 and 23° C.

5. A polyoxyalkylene derivative according to claim 1, wherein Z is a residue of a compound having 3 to 8 hydroxyl groups, and a and b satisfy the relationship: $3 \leq a+b \leq 8$.

6. A polyoxyalkylene derivative according to claim 2, wherein Z is a residue of a compound having 3 to 8 hydroxyl groups, and a and b satisfy the relationship: $3 \leq a+b \leq 8$.

7. A polyoxyalkylene derivative according to claim 3, wherein Z is a residue of a compound having 3 to 8 hydroxyl groups, and a and b satisfy the relationship: $3 \leq a+b \leq 8$.

8. A polyoxyalkylene derivative according to claim 1, which is used for modification of a biological substance.

9. A polyoxyalkylene derivative according to claim 1, wherein X is a divalent hydrocarbon group having 3 carbon atoms.

10. A polyoxyalkylene derivative according to claim 2, wherein X is a divalent hydrocarbon group having 3 carbon atoms.

11. A polyoxyalkylene derivative according to claim 3, wherein X is a divalent hydrocarbon group having 3 carbon atoms.

12. A process for producing a polyoxyalkylene derivative represented by formula (I):

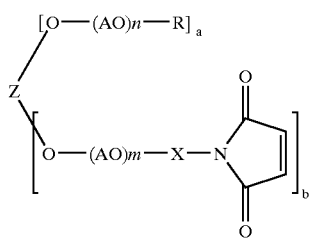

(I)

wherein Z represents a residue of a compound having 2 to 8 hydroxyl groups; AO represents an oxyalkylene group having 2 to 18 carbon atoms; n and m each represent an integer of 0 to 2000 provided that both n and m do not represent 0; a and b each represent an integer satisfying the relationships: $2 \leq a+b \leq 8$ and $1 \leq b$; R represents a hydrocarbon group having 1 to 30 carbon atoms; and X represents a divalent hydrocarbon group having 3 to 10 carbon atoms, the process comprising:
allowing an amino-terminated polyoxyalkylene derivative represented by formula (III):

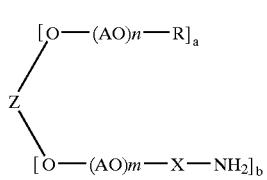

(III)

wherein Z, AO, n, m, a, b, R, and X are as defined above, to react with maleic anhydride to form a maleamic acid-terminated polyoxyalkylene derivative represented by formula (IV):

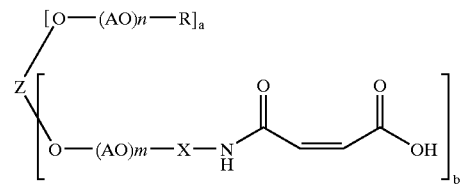

(IV)

wherein Z, AO, n, m, a, b, R, and X are as defined above;
dissolving the compound represented by formula (IV) in 50 to 500 vol/wt %, based on the compound represented by formula (IV), of an organic solvent;
crystallizing the compound represented by formula (IV) from 300 to 5000 vol/wt %, based on the compound represented by formula (IV), of a mixture of ethyl acetate and n-hexane; and
imidizing a maleamic acid end group of the compound represented by formula (IV).

13. A process for producing a polyoxyalkylene derivative represented by formula (I):

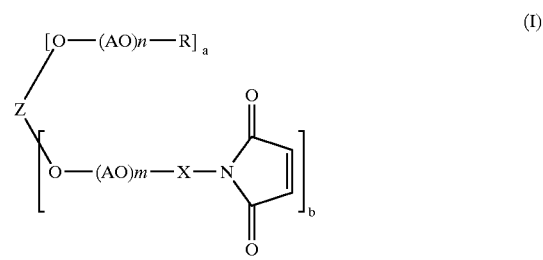

(I)

wherein Z represents a residue of a compound having 2 to 8 hydroxyl groups; AO represents an oxyalkylene group having 2 to 18 carbon atoms; n and m each represent an integer of 0 to 2000 provided that both n and m do not represent 0; a and b each represent an integer satisfying the relationships: $2 \leq a+b \leq 8$ and $1 \leq b$; R represents a hydrocarbon group having 1 to 30 carbon atoms; and X represents a divalent hydrocarbon group having 3 to 10 carbon atoms, the process comprising:
converting a hydroxyl-terminated polyoxyalkylene derivative represented by formula (II):

(II)

wherein Z, AO, n, m, a, b, and R are as defined above, to an amino-terminated polyoxyalkylene derivative represented by formula (III):

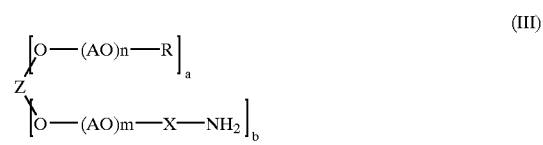

(III)

wherein Z, AO, n, m, a, b, and R are as defined above; and X represents a divalent hydrocarbon group having 3 to 10 carbon atoms, by cyanation followed by hydrogenation;

allowing the compound represented by formula (III) to react with maleic anhydride to form a maleamic acid-terminated polyoxyalkylene derivative represented by formula (IV):

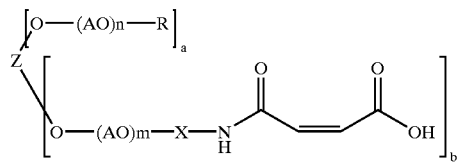

(IV)

wherein Z, AO, n, m, a, b, R, and X are as defined above;

dissolving the compound represented by formula (IV) in 50 to 500 vol/wt %, based on the compound represented by formula (IV), of an organic solvent;

crystallizing the compound represented by formula (IV) from 300 to 5000 vol/wt %, based on the compound represented by formula (IV), of a mixture of ethyl acetate and n-hexane; and imidizing a maleamic acid end group in the compound represented by formula (IV).

14. A process for producing a polyoxyalkylene derivative according to claim 12, wherein the maleamic acid-terminated polyoxyalkylene derivative represented by formula (IV) has a maleic anhydride content of 0.5 wt % or less.

15. A process for producing a polyoxyalkylene derivative according to claim 13, wherein the maleamic acid-terminated polyoxyalkylene derivative represented by formula (IV) has a maleic anhydride content of 0.5 wt % or less.

* * * * *